United States Patent
Fazzi et al.

(10) Patent No.: US 9,436,873 B2
(45) Date of Patent: Sep. 6, 2016

(54) METHOD AND SYSTEM FOR MONITORING THE SKIN COLOR OF A USER

(75) Inventors: Alberto Fazzi, Eindhoven (NL); Jeroen Veen, Nijmegen (NL); Mohammed Meftah, Tilburg (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 303 days.

(21) Appl. No.: 14/117,688
(22) PCT Filed: May 25, 2012
(86) PCT No.: PCT/IB2012/052630
§ 371 (c)(1),
(2), (4) Date: Nov. 14, 2013
(87) PCT Pub. No.: WO2012/164462
PCT Pub. Date: Dec. 6, 2012

(65) Prior Publication Data
US 2014/0078301 A1 Mar. 20, 2014

(30) Foreign Application Priority Data
May 31, 2011 (EP) .................................. 11168286

(51) Int. Cl.
*G06K 9/00* (2006.01)
*A61B 5/00* (2006.01)
(Continued)

(52) U.S. Cl.
CPC ......... *G06K 9/00671* (2013.01); *A61B 5/0059* (2013.01); *A61B 5/1032* (2013.01);
(Continued)

(58) Field of Classification Search
CPC ...... H04N 7/181; H04N 7/183; H04N 7/186; H04N 7/18; H04N 7/188; H04N 1/62; H04N 5/23248; H04N 9/643; H04N 5/228; H04N 5/23212; G08B 13/19656; A61B 5/103; A61B 5/0059; A61B 5/1032; A61B 5/441; A61B 18/20; A61B 5/00; A61B 5/4041; A61B 5/4824; F21V 23/04; A61N 5/0616; G06F 3/033; G03F 3/08

See application file for complete search history.

(56) References Cited

U.S. PATENT DOCUMENTS 6,679,830 B2 * 1/2004 Kolarovic .............. A61G 11/00
600/22
(Continued)

FOREIGN PATENT DOCUMENTS

| JP | 11076434 | 3/1999 |
| WO | WO9641140 | 6/1996 |

(Continued)

OTHER PUBLICATIONS

Sigal et al. Skin Color-Based Video Segmentation under Time-Varying Illumination, IEEE Transactions on Pattern Analysis and Machine Intelligence, vol. 26, No. 6, Jun. 2004.*

(Continued)

*Primary Examiner* — Jay Au Patel
*Assistant Examiner* — Frank Huang

(57) ABSTRACT

This invention relates to a method and a system for monitoring skin color of a user. The system comprises a capturing unit, an obtaining unit, a deriving unit and a determining unit. The capturing unit captures at least one image of the user over a predetermined time period, and the obtaining unit obtains motion-related information of the user over the predetermined time period. The deriving unit derives visual information from the at least one image on the basis of the motion-related information, and the determining unit determines the skin color on the basis of the derived visual information. In this way, the skin color of the user can be effectively monitored without exposing the user to strong environmental light.

20 Claims, 2 Drawing Sheets

(51) Int. Cl.
*A61B 5/103* (2006.01)
*G01J 3/50* (2006.01)
*G06T 7/20* (2006.01)
*A61G 11/00* (2006.01)

(52) U.S. Cl.
CPC ............... *A61B 5/441* (2013.01); *G01J 3/50* (2013.01); *G06T 7/20* (2013.01); *A61B 2503/045* (2013.01); *A61G 11/00* (2013.01)

(56) References Cited

U.S. PATENT DOCUMENTS

| | | | | |
|---|---|---|---|---|
| 7,872,670 | B2* | 1/2011 | Kikuchi | H04N 5/23212 348/157 |
| 2004/0249290 | A1* | 12/2004 | Shani | A61B 5/0059 600/476 |
| 2005/0027336 | A1* | 2/2005 | Nemenov | A61B 5/0059 607/98 |
| 2005/0212950 | A1* | 9/2005 | Kanai | H04N 5/23212 348/345 |
| 2006/0089546 | A1 | 4/2006 | Mahony et al. | |
| 2006/0139707 | A1* | 6/2006 | Kimura | H04N 1/62 358/518 |
| 2007/0217199 | A1* | 9/2007 | Adam | A61N 5/0616 362/276 |
| 2008/0120577 | A1* | 5/2008 | Ma | G06F 3/0325 715/863 |
| 2008/0136958 | A1* | 6/2008 | Nakahara | G06K 9/00255 348/345 |
| 2008/0194906 | A1 | 8/2008 | Mahony et al. | |
| 2008/0292151 | A1 | 11/2008 | Kurtz et al. | |
| 2008/0294012 | A1* | 11/2008 | Kurtz | A61B 5/0059 600/300 |
| 2009/0196475 | A1 | 8/2009 | Demirli et al. | |
| 2010/0007746 | A1 | 1/2010 | Lee | |
| 2010/0322300 | A1* | 12/2010 | Li | G06K 9/00234 375/240.01 |
| 2015/0230863 | A1* | 8/2015 | Youngquist | A61B 18/203 606/9 |

FOREIGN PATENT DOCUMENTS

| | | |
|---|---|---|
| WO | WO9719341 | 5/1997 |
| WO | WO9931472 | 6/1999 |
| WO | WO2010061493 | 6/2010 |

OTHER PUBLICATIONS

Konica Minolta, "Highly Accurate Measure of Skin Color", CM-SA-Specialty Meters/Medical/Personal Care/Konica Minolta, 2007-2010, webpage downloaded on Oct. 28, 2010.

* cited by examiner

METHOD AND SYSTEM FOR MONITORING THE SKIN COLOR OF A USER

CROSS-REFERENCE TO PRIOR APPLICATIONS

This application is the U.S. National Phase application under 35 U.S.C. §371 of International Application Serial No. PCT/IB2012/052630, filed on May 25, 2012, which claims the benefit of European Application Serial No. 11168286.0, filed on May 31, 2011. These applications are hereby incorporated by reference herein.

FIELD OF THE INVENTION

The invention relates to a method and a system for monitoring the skin color of a user, particularly a method and a system for monitoring the skin color of a neonate.

BACKGROUND OF THE INVENTION

It is common practice in neonatal intensive care units (NICU) to visually monitor and evaluate skin color of a neonate to have an indication of the neonate's physiopathologic conditions. For example, skin color provides indications of blood circulation, temperature and stress response of the neonate.

It is also common practice to shield the neonate, especially a premature neonate, from strong environmental light to avoid damage to eyes and to reduce the level of stress. The necessity of reducing exposure to light is recognized by the medical community and results in two main practices: having dimmed light within the NICU, and/or applying a cover to an incubator to provide shielding from light in the NICU environment.

However, the dimmed light will highly degrade the accuracy of skin color monitoring. Furthermore, while shielding the neonate from environmental light, the cover of the incubator also hinders visual monitoring of the neonate, and therefore, the cover needs to be periodically opened or removed to evaluate skin color.

While the monitoring of movements in the dark could be easily accomplished by simply using available infra-red cameras, there is currently no solution for monitoring skin color in the absence of light or at an extremely reduced light intensity.

U.S. Pat. No. 6,679,830 B2 discloses an infant care unit and suggests using video cameras to monitor physiological parameters such as skin color. However, it does not disclose how to monitor skin color of a neonate when the neonate is within the infant care unit which is generally kept very dark to protect the neonate.

SUMMARY OF THE INVENTION

Based on the understanding of the technical problems and prior art described above, it would be desirable to monitor skin color of a user without exposing the user to strong environmental light. It would also be desirable to monitor the skin color of a neonate inside an incubator with little to no light within the incubator and without the need to open the cover of the incubator. It would further be desirable to effectively control skin color monitoring so as to reduce disturbance of the user and well-being risks to the user.

To better address one or more of the above concerns, in an embodiment of a first aspect of the invention, a system for monitoring skin color of a user illuminated by a light source is provided. The system comprises:

a capturing unit for capturing at least one image of the user over a predetermined time period;

an obtaining unit for obtaining motion-related information of the user over the predetermined time period;

a deriving unit for deriving visual information from the at least one image on the basis of the motion-related information; and a determining unit for determining the skin color on the basis of the visual information.

At least one image is captured over a predetermined time period. Skin color can be detected on the proviso that a sufficient amount of reflected light from the skin of the user is accumulated, in time, during the predetermined period. Furthermore, since information about the user's motion, i.e. the so-called motion-related information, is obtained and then used for deriving visual information, distortion caused by the user's motions during the predetermined time can be mitigated. The distortion comprises an image being blurred due to the user's motion during the acquisition time when light information is being accumulated, and/or visual information derived from a plurality of images and being inaccurate because the position of the user in the plurality of the images changes due to the user's motions. Since the skin color is determined on the basis of the visual information derived from the at least one image, and the at least one image is captured over the predetermined period time, each measurement of the skin color approximately takes the predetermined period of time. However, considering that the skin color does not change rapidly, such a period of time is acceptable for monitoring the color of the skin.

According to another embodiment, the system further comprises a first controlling unit for controlling the direction and/or the beam size of the light source to focus the light from the light source on a predefined part of the user.

The predefined part of the user can refer to any specific part or spot of the user's body that is relevant and representative to be used for performing a measurement of the skin color.

In comparison with light diffusion over the user, when the light is focused on a predefined part of the user, the amount of light entering the visual space of the user can be reduced while the illumination of the predefined part remains the same. Thus, the disturbance of and risk of damage to the user can be reduced accordingly. Alternatively, by focusing the light on the predefined part of the user, the illumination of the predefined part can be increased while the amount of light entering the visual space of the user remains the same, thereby maintaining the same comfort level for the user. Thus, the predetermined time period for light accumulation can be reduced accordingly, and in turn the time consumption as well as the distortion due to the user's motions can be reduced also.

According to another embodiment, the system further comprises a detecting unit for detecting the status of the user, and a second controlling unit for controlling the illumination intensity of the light source according to the detected status of the user.

For example, the status of the user comprises the status of the eyes of the user, and/or discomfort signs that indicate the discomfort of the user. When the eyes of the user are closed, the illumination intensity can be relatively increased and, in turn, the predetermined time period can be decreased compared to the scenario where the eyes of the user are open.

In this way, a good trade-off between the comfort level of the user and the effectiveness of the skin monitoring, such as time consumption and accuracy, can be adaptively achieved.

According to yet another embodiment, the system further comprises the light source, and the light source and the capturing unit are integrated into at least one of the following: mattress intended to be placed under the user, and clothing of the user. Additionally or alternatively, the light source and the capturing unit are attachable to the user.

In this way, the illumination can be highly localized and therefore, high illumination of the user's skin can be achieved without causing any disturbance to the user.

In an embodiment of a second aspect of the invention, a method of monitoring skin color of a user illuminated by a light source is provided. The method comprises the steps of:

capturing at least one image of the user over a predetermined time period;

obtaining motion-related information of the user over the predetermined time period;

deriving visual information from the at least one image on the basis of the motion-related information; and determining the skin color on the basis of the visual information.

These and other aspects of the invention will be apparent from and elucidated with reference to the embodiments described hereinafter.

DESCRIPTION OF THE DRAWINGS

The above and other objects and features of the present invention will become more apparent from the following detailed description considered in connection with the accompanying drawings, in which.

The same reference numerals are used to denote similar parts throughout the figures.

DETAILED DESCRIPTION

Figure 1:
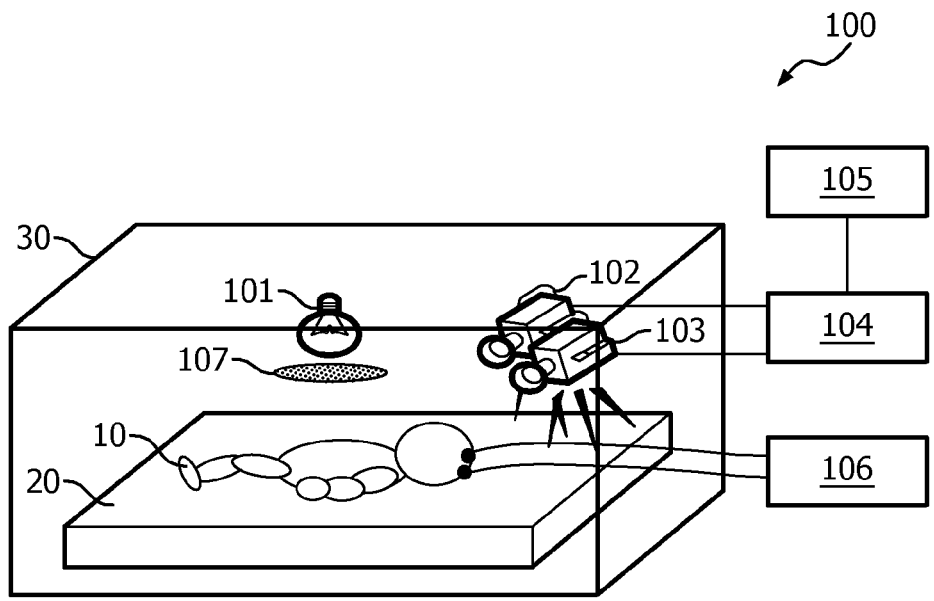
FIG. 1 shows a schematic diagram of an exemplary application scenario of a system in accordance with an embodiment of the invention.

FIG. 1 shows a schematic diagram of an exemplary application scenario of a system 100 in accordance with an embodiment of the invention.

The system 100 is configured to monitor skin color of a user illuminated by a light source. The system 100 can be applied for any kinds of person who need a skin color measurement or monitoring, such as adults, children and neonates. The advantages of the system are more obvious when the light intensity of the light source is low. For example, premature neonates will be disturbed or even injured by strong environmental light, so the light source illuminating the premature neonates should have a low light intensity. Preferably, the light emitted by the light source has a sufficiently wide and distributed spectrum in the visible range to enable correct color determination. Moreover, it can be beneficial to optimize the spectrum of the emitted light so that it causes as little stress as possible to the neonate.

According to an embodiment of the invention, the system 100 is applied to monitor skin color of a neonate.

Referring to FIG. 1, a neonate 10 is lying on a mattress 20 within an incubator 30. The incubator 30 is generally kept as dark as possible for the purpose of reducing the stress for the neonate and the risk of eye damage. A light source 101 within the incubator 30 can be configured to provide diffused light with a low intensity; the intensity should be so low that the neonate is not disturbed. The system 100 can comprise the light source 101. Alternatively, the light source 101 can be a stand-alone device.

Further, referring to FIG. 1, the system 100 comprises a capturing unit 102 for capturing at least one image of the user over a predetermined time period. The capturing unit 102 can be a photo camera, a video camera, a light detector, or the like. The at least one image can show the whole body of the user or part of the user's body. The predetermined time period can be related to the light intensity of the light source 101. For example, when the light intensity is lower, the predetermined time period is set to be longer so as to accumulate a sufficient amount of the reflected light from the user's skin for determination of the skin color. Furthermore, the number of the at least one image can be set according to the user's skin monitoring requirements. For example, when the number of the at least one image is smaller, a smaller number of images need to be processed to derive the visual information for skin color determination and the complexity of the skin monitoring operation can therefore be reduced. In another example, when the number of the at least one image is larger, a higher flexibility can be provided when the visual information for skin color determination is derived, and the skin monitoring accuracy can be enhanced.

The capturing unit 102 can be configured to capture the at least one image in different ways.

In one embodiment, the capturing unit 102 captures an image at a point in time, with the shutter time being equal to or slightly smaller than the predetermined time period. The shutter time, also known as exposure time, represents the time it takes for light to reach the film or image sensor. By having a sufficiently long exposure time, the reflected light from the user will be accumulated over the exposure time, resulting in a single correctly exposed image.

In another embodiment, the capture unit 102 captures more than one image at a series of time points, and the total acquisition time of the more than one image is equal to the predetermined time period. The captured images will then be processed to accumulate visual information across these images to obtain a single correctly exposed image, which will be described later.

When the user moves during the image capturing process, the image will be bluffed. Additionally, when the user moves during the capturing of a plurality of images, the position of the user's body will change across the plurality of images. Thus, the user's motion might make the skin color measurement less reliable.

In order to obtain information about the user's motion, the system 100 further comprises an obtaining unit 103 for obtaining motion-related information of the user over the predetermined time period. An example of such a unit could be an infra-red camera capable of visualizing movement of the user in a condition of extremely low light intensity.

The motion-related information can comprise any kind of information about the user's motion. In one embodiment, taking into consideration that a neonate, especially a premature neonate, mostly moves the limbs while other parts of the body remain mostly still, the motion-related information comprises a motion indication for each part of the user's body to indicate whether the part of the user's body moves in the image or not, or to further indicate the motion level. Additionally, the motion-related information comprises a motion indication for each image. In another embodiment, the motion-related information comprises information about the position of the user's body in each image and/or information about changes of the user's body position in different images. For example, when the left hand of the user moves from a first position in a first image to a second position in a second image, the motion-related information comprises the first position and the second position. Alternatively, the motion-related information may comprise the first position and the difference between the first and the second position.

The obtaining unit 103 can obtain the motion-related information in different ways. In one embodiment, the obtaining unit 103 comprises a motion detector for detecting the user's motion. The motion detector can be an infra-red camera, a passive infra-red sensor, an accelerometer attached to the user or a pressure sensor integrated in the mattress or just below the mattress. In another embodiment, the obtaining unit 103 comprises a processor for obtaining the motion-related information by means of image processing. Various image processing techniques can be applied. For example, blurred areas of an image can be identified by detecting edges and boundaries. For another example, different parts of the user's body can be identified by a pattern recognition technique. On the basis of the identified different parts, the positions of each part in each image and/or the changes of the positions across a plurality of images can then be determined.

The system 100 further comprises a deriving unit 104 for deriving visual information from the at least one image on the basis of the motion-related information. The visual information refers to any information about the reflected light of the user captured in the at least one image. For example, when the deriving unit is provided with one image, the visual information can be the whole image or part of the image. In another example, when the deriving unit is provided with more than one image, the visual information can be an image generated by accumulating the more than one image.

The deriving unit 104 can derive the visual information in different ways.

In one embodiment, the deriving unit 104 selects non-bluffed or less-blurred areas from an image and only uses the selected areas to derive the visual information for determining the skin color. Additionally or alternatively, when more than one image is provided, the deriving unit 104 selects non-bluffed or less-bluffed images from a plurality of images and uses only the selected images. For example, the selection can be performed on the basis of the motion indications provided by the obtaining unit 103.

In another embodiment, when the deriving unit 104 is provided with more than one image, it generates an image by accumulating the visual information across the more than one image therein by means of image processing. For example, the generated image is a superposition of the more than one image. Preferably, the deriving unit 104 can further use any algorithm known by the person skilled in the art for motion estimation and/or motion compensation to correct the distortion during the accumulating procedure. For example, the deriving unit 104 can use the algorithm to maximize the quality of the generated image. Additionally or alternatively, the deriving unit 104 can identify those parts of the more than one image in which the user does not move, or not move excessively, and apply the derivation procedure only to those.

Additionally, the deriving unit 104 can further evaluate the quality of the generated image, and judge, for the generated image or for different parts of the generated image, whether there is sufficient visual information for a reliable skin color measurement. If the quality of parts of the generated image is not good enough for a reliable measurement, these parts of the generated images will be identified and will not be used for skin color determination.

The system 100 further comprises a determining unit 105. The determining unit 105 is configured to determine skin color on the basis of the visual information derived by the deriving unit 104. For example, the determining unit 105 can identify, from the image output by the deriving unit 104, which part contains skin and determine the skin color.

The system 100 further comprises a first controlling unit. The first controlling unit is configured to focus the light from the light source 101 on a predefined part of the user. For example, the first controlling unit can comprise a lighting controller, a light adjuster or the like. Preferably, the first controlling unit can control the direction and/or beam size of the light from the light source 101 on the basis of the motion-related information obtained by the obtaining unit 103, such as the user's position or the position of a predefined part of the user. In this way, the light can be focused on the predefined part of the user, even if its position changes due to the user's motions. Additionally, the light intensity can be also controlled in accordance with the predefined part to be illuminated. Preferably, the predefined part of the user comprises a part of the user's skin that is relevant and representative for performing a skin color monitoring process.

In this way, the percentage of the light emitted from the light source that enters the visual space of the user can be decreased. In comparison with the case where diffusing light is used, if the light is focused on the desired part of the user, it is possible to use stronger light while still maintaining the same level of comfort for the user. Accordingly, the image acquisition time can be reduced, and, in turn, distortion due to the user's motion during the predetermined time can be reduced as well.

Additionally, the first controlling unit can be further configured to be switchable between a mode of focusing the light from the light source on the desired part of the user and a mode of diffusing the light over the user.

The system 100 further comprises a detecting unit for detecting the status of the user, and a second controlling unit for controlling an illumination intensity of the light source 101 according to the detected status of the user. The status of the user can be one of the following, but is not limited thereto: the status of the user's eyes, and one or more discomfort signs. The status of the user's eyes refers to whether the eyes are open or closed. The discomfort signs comprise any sign indicating the discomfort of the user. The discomfort signs can be associated with eye blinking, eye movements or other parameters such as the amount of the user's motion and the type of motion. As an example of the functionality of this second controlling unit, when the user's eyes are open, the second controlling unit reduces the illumination intensity of the light source 101. Alternatively, the light source 101 shuts down when the user's eyes are open. To the contrary, when the user's eyes are closed, the illumination intensity of the light source 101 is increased and image acquisition time can be reduced while still obtaining sufficient visual information for skin color determination. In another example, when discomfort signs are detected, the illumination intensity of the light source 101 is reduced to a level at which the discomfort signs disappear or fall within a predefined range.

The detecting unit can detect the status of the user in many ways. In an embodiment, infra-red imaging is used to detect the status of the eyes of the neonate, i.e. whether the eyes are open or closed. Infra-red imaging can be also used to detect the user's motion. When the obtaining unit 103 comprises a motion detector such as an infra-red camera, the detecting unit can comprise the same motion detector or in fact use the output information of said detector. Additionally or alternatively, the user is further monitored by an electrophysiological monitor 106, as shown in FIG. 1. In this case, the status of the user can be detected according to Electroencephalogram (EEG) signals or Electrooculargram (EOG) signals. For example, an increase of alpha waves is known to be observed when the eyes are closed. Moreover, EOG signals are known to give an indication of eye movements.

The illumination intensity of the light source can be controlled using different techniques, such as in mechanical way or an optoelectronic way. In an embodiment, the light intensity of the light source is directly controlled to control the illumination intensity. For example, the second controlling unit can comprise a lighting controller, a light adjuster or the like. Referring to FIG. 1, in another embodiment, the second controlling unit comprises a controllable unit 107 such as an adjustable shutter, a focusing element or a combination thereof. The controllable unit 107 is positioned in front of the light source and the illumination over the user is controlled by controlling the light passing through the controllable unit 107.

Figure 2:
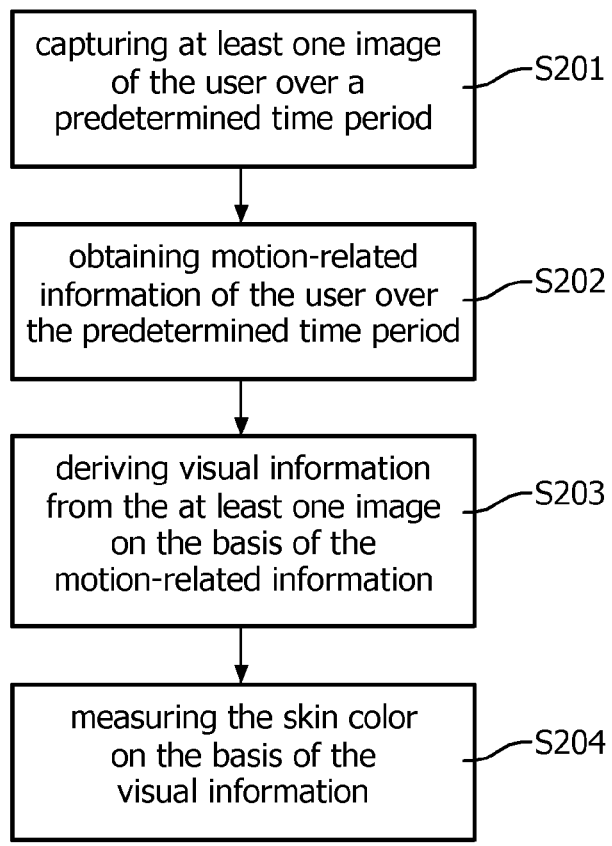
FIG. 2 shows a flowchart of a method in accordance with an embodiment of the invention.

FIG. 2 shows a flowchart of a method in accordance with an embodiment of the invention.

According to an embodiment of the present invention, a description is given of a method of monitoring the color of a user's skin which is illuminated by a light source.

Referring to FIG. 2, the method comprises step 201 of capturing at least one image of the user over a predetermined time period.

The method further comprises step 202 of obtaining motion-related information of the user over the predetermined time period. For example, said step 202 comprises a sub-step of obtaining the motion-related information by detecting the user's motion. Additionally or alternatively, the step 202 comprises a sub-step of obtaining the motion-related information by means of image processing.

The method further comprises step 203 of deriving visual information from the at least one image on the basis of the motion-related information. For example, said step 203 comprises the following sub-steps: selecting areas from a plurality of areas of the at least one image on the basis of the motion-related information obtained in step 202, and deriving the visual information from the selected areas. Additionally, when the at least one image comprises more than one image, the step S203 comprises a sub-step of deriving the visual information by accumulating the visual information across the more than one images.

The method further comprises step 204 of determining skin color on the basis of the visual information derived in step 203.

Moreover, steps 201 to 204 can be repeated to measure or monitor the skin color of the user at different times. For example, steps 201 to 204 can be repeated periodically, and the period can be set according to the skin color monitoring requirements of the user. For example, the period can be set to be short when the user requires intensive monitoring due to the user's unstable condition.

Additionally, the method can further comprise a step of controlling the direction and/or beam size of the light source to focus the light from the light source on a predefined part of the user. Furthermore, the method can comprise a step of controlling the illumination intensity of the light source according to a status of the user FIG. 3 shows a schematic diagram of an exemplary application scenario of a system in accordance with another embodiment of the invention.

Figure 3:
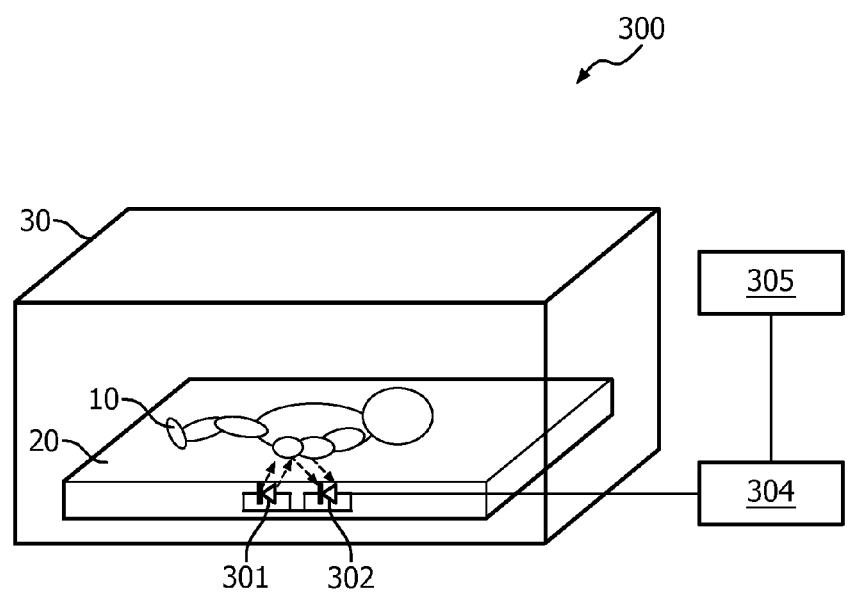
FIG. 3 shows a schematic diagram of an exemplary application scenario of a system in accordance with another embodiment of the invention.

Referring to FIG. 3, the system 300 comprises a light source 301, a capturing unit 302, a deriving unit 304 and a determining unit 305. The light source 301 can be one or more LEDs; for the capturing unit 302 use can be made of photodiodes or other kind of sensors detecting the color of reflected light. The light source 301 is configured to direct the illumination to a measuring point; the capturing unit 302 is configured to capture the at least one image of the measuring point; the deriving unit 304 is configured to derive visual information about the user's skin at the measuring point from the captured at least one image; and the determining unit 305 is configured to determine the skin color of the user at the measuring point according to the derived visual information.

For example, the light source 301 and the capturing unit 302 are positioned at the measuring point. In another example, the light source 301 and the capturing unit 302 are light guides such as optical fibers. The light guides guide the light of an external light source to the measuring point and guide the reflected light at the measuring point to an external light detector.

In this way, the illumination can be highly localized and, therefore, a high illumination level on the user's skin can be achieved without causing any disturbance to the user.

In an embodiment, the light source 301 and the capturing unit 302 are integrated into at least one of the following: mattress 20 intended to be placed under the user, clothing of the user, and any other objects intended to be placed in the proximity of the user.

Further, the system 100 can comprise an array of pairs of such light sources 301 and capturing units 302. Each pair of the light sources 301 and capturing units 302 can be used to monitor the skin color at various measuring points.

Preferably, the system 100 comprises a third controlling unit for controlling the light sources 301 at the various measuring points so as to eliminate or reduce the risk of shining glaring light into the eyes of the user. For example, the third controlling unit identifies the light sources positioned near the head of the user on the basis of position information about the user, and shuts down the identified light sources. In this case, the system can further comprise an additional unit which is identical or similar to the obtaining unit 103 in FIG. 1 to obtain the position information about the user, such as the position of the user with respect to the light sources 301.

In another embodiment, the light source 301 and the capturing unit 302 are attachable to the user.

In this way, skin monitoring can be performed at standardized positions with a more reproducible optical interface and the user's motion has little to no impact, leading to highly reliable and reproducible measurements.

For example, the light source 301 and the capturing unit 302 can be directly attached to the user's body via a holding fixture such as a band.

In another example, the light source 301 and the capturing unit 302 can be integrated into a wearable device. The integration into an existing type of devices such as a SPO2 sensing device is particularly attractive. A neonate inside a NICU is normally monitored with the SPO2 sensing device. Thus, the skin color of the neonate can be monitored without attaching any additional device or sensor to the neonate A set of computer-executable instructions is further proposed to perform the methods described above. The instructions can reside in the obtaining unit, the deriving unit, the determining unit, the first controlling unit, the second controlling unit and/or the third controlling unit, to perform any step of the above disclosed methods.

Although the present invention will be described with reference to the embodiment shown in the drawings, it should be understood that the present invention may be embodied in many alternate forms including any combination of hardware and software. In addition, any suitable size, shape or type of materials, elements, computer program elements, computer program codes, or computer program modules could be used.

While discussed in the context of computer program code, it should be understood that the modules may be implemented in hardware circuitry, computer program code, or any combination of hardware circuitry and computer program code.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the system claims enumerating several units, several of these units can be embodied by one and the same item of hardware or software. The use of the words first, second and third, et cetera, does not indicate any ordering. These words are to be interpreted as names.

The invention claimed is:

1. A system for monitoring the skin color of a user, the system comprising:
 a light source configured to emit light to illuminate skin of the user;
 a first controller configured to control at least one of a direction and a beam size of the light source to focus the light from the light source on a predefined part of the user;
 a capturing device configured to capture at least one image of the user over a predetermined time period, the predetermined time period being determined by at least one of the direction and the beam size of the light emitted from the light source;
 an obtaining device configured to obtain motion-related information of the user over the predetermined time period; and
 one or more processors programmed to:
  derive visual information from the at least one image on the basis of the motion-related information; and
  determine the skin color on the basis of the visual information.

2. The system as claimed in claim 1, wherein the obtaining device comprises:
 a motion detector configured to obtain the motion-related information by detecting the motion of the user.

3. The system as claimed in claim 1, wherein the obtaining device comprises:
 a processor programmed to obtain the motion-related information by image processing.

4. The system as claimed in claim 1, wherein:
 the one or more processor is programmed to:
  select areas from a plurality of areas of the at least one image on the basis of the motion-related information; and
  derive from the selected areas information from the at least one image based on the obtained motion-related information to determine one or more distorted portions and one or more non-distorted portions in the at least one image caused by motion of the user.

5. The system as claimed in claim 1, wherein:
 the at least one image comprises more than one image; and
 the one or more processor is programmed to derive the visual information by accumulating the visual information across the more than one image.

6. The system as claimed in claim 1, further comprising:
 a detector configured to detect a status of the user; and
 a second controller configured to control the illumination intensity of the light source according to the detected status of the user.

7. The system as claimed in claim 1, wherein:
 the light source and the capturing device are integrated into at least one of:
  a mattress configured to be placed under the user; and
  clothing configured to be worn by the user.

8. The system as claimed in claim 1, wherein:
 the light source and the capturing device are configured to be attachable to the user.

9. A method of monitoring skin color of a user illuminated by a light source, the method comprising:
 with a first controller, controlling the direction and/or beam size of the light source to focus the light from the light source on a predefined part of the user;
 with a capturing device, capturing at least one image of the user over a predetermined time period, the predetermined time period being determined by at least one of the direction and the beam size of the light emitted from the light source;
 with an obtaining device, obtaining motion-related information of the user over the predetermined time period;
 with one or more processors, deriving visual information from the at least one image on the basis of the motion-related information; and
 with the one or more processors, determining the skin color on the basis of the visual information.

10. The method as claimed in claim 9, wherein the obtaining further includes:
 obtaining the motion-related information by detecting the motion of the user.

11. The method as claimed in claim 9, wherein the obtaining further includes:
 obtaining the motion-related information by image processing.

12. The method as claimed in claim 9, wherein the deriving further includes:
 selecting areas from a plurality of areas of the at least one image on the basis of the motion-related information; and
 deriving from the selected areas visual information from the at least one image based on the obtained motion-related information to determine one or more distorted portions and one or more non-distorted portions in the at least one image caused by motion of the user.

13. The method as claimed in claim 9, wherein:
 the at least one image comprises more than one images; and
 the deriving further includes deriving the visual information by accumulating the visual information across the more than one images.

14. A set of computer-executable instructions, configured to perform the method of claim 9.

15. The method as claimed in claim 9, further comprising:
with a detector, detecting a status of the user; and
with a second controller, controlling the illumination intensity of the light source according to the detected status of the user.

16. An apparatus for monitoring skin color, the apparatus comprising:
a light source configured to emit light to illuminate skin of a user;
a first lighting controller configured to control the intensity of the emitted light by adjusting at least one of a direction and a beam size of the light source to focus the emitted light on a predefined part of the user;
an optical camera configured to capture at least one image of at least a portion of the predefined part of the user over a predetermined time period, the predetermined time period being inversely proportional to the light intensity of the emitted light;
an infrared camera configured to obtain motion-related information of the user over the predetermined time period; and
at least one processor programmed to:
derive visual information from the at least one image based on the obtained motion-related information to determine one or more distorted portions and one or more non-distorted portions in the at least one image that is captured by the optical camera caused by motion of the user; and
determine the skin color based on the one or more non-distorted portions in the at least one image.

17. The apparatus as claimed in claim 16, wherein infrared camera includes at least one of:
a motion detector configured to obtain the motion-related information by detecting motion of the user; and
wherein the at least one processor is further programmed to obtain the motion-related information by analyzing the at least one image.

18. The apparatus as claimed in claim 16, wherein the at least one processor is programmed to:
select at least one area from a plurality of areas of the at least one image based on the obtained motion-related information; and
derive the one or more distorted portions and one or more non-distorted portions in the at least one image from the selected areas.

19. The apparatus as claimed in claim 16, further including:
a detector configured to detect a status of the user, the status including at least one of open eyes, closed eyes, blinking, and eye movement of the user; and
an adjustable shutter controller configured to control the illumination intensity of the light source responsive to the detected status of the user.

20. The apparatus as claimed in claim 19, further including:
an electrophysiological monitor configured to detect at least one of electroencephalogram signals and electrooculargram signals, the electroencephalogram signals and electrooculargram signals being indicative of the status of the user.

* * * * *